US008337895B2

(12) United States Patent
Bennett et al.

(10) Patent No.: US 8,337,895 B2
(45) Date of Patent: Dec. 25, 2012

(54) SPRAY DRYING PROCESS CONTROL OF DRYING KINETICS

(75) Inventors: David B Bennett, Cupertino, CA (US); Thomas K Brewer, Boonville, CA (US); Robert M Platz, Half Moon Bay, CA (US); Herman Snyder, Pacifica, CA (US)

(73) Assignee: Novartis AG, Basel (CH)

( * ) Notice: Subject to any disclaimer, the term of this patent is extended or adjusted under 35 U.S.C. 154(b) by 703 days.

(21) Appl. No.: 12/462,209

(22) Filed: Jul. 29, 2009

(65) Prior Publication Data

US 2010/0034910 A1   Feb. 11, 2010

Related U.S. Application Data

(63) Continuation of application No. 09/733,269, filed on Dec. 8, 2000, now Pat. No. 7,575,761, which is a continuation-in-part of application No. 09/607,975, filed on Jun. 30, 2000, now abandoned.

(51) Int. Cl.
*A61K 9/14* (2006.01)

(52) U.S. Cl. ........................................................ 424/489

(58) Field of Classification Search ........................ None
See application file for complete search history.

(56) References Cited

U.S. PATENT DOCUMENTS

| | | | |
|---|---|---|---|
| 2,598,525 A | 4/1950 | Fox | |
| 2,911,036 A * | 11/1959 | Lazar et al. ................. | 159/4.01 |
| 3,362,405 A | 4/1964 | Hazel | |
| 3,425,600 A | 8/1966 | Abplanalp | |
| 3,300,868 A * | 1/1967 | Fritz .............................. | 34/291 |
| 3,313,032 A * | 4/1967 | Malecki ........................ | 34/288 |
| 3,674,901 A | 7/1972 | Shepherd et al. | |
| 3,770,207 A | 11/1973 | Muller et al. | |
| 3,790,079 A | 2/1974 | Berglund et al. | |
| 3,825,188 A | 7/1974 | Doering | |
| 3,921,637 A | 11/1975 | Bennie et al. | |
| 3,956,009 A | 5/1976 | Lundquist et al. | |
| 3,964,483 A | 6/1976 | Mathes | |
| 3,991,304 A | 11/1976 | Hillsman | |
| 3,991,761 A | 11/1976 | Cocozza | |
| 3,994,421 A | 11/1976 | Hansen | |
| 4,035,317 A | 7/1977 | Gershberg | |
| 4,036,223 A | 7/1977 | Obert | |
| 4,052,255 A | 10/1977 | Hackbarth et al. | |
| 4,069,819 A | 1/1978 | Valentini et al. | |
| 4,098,273 A | 7/1978 | Glenn | |
| 4,127,235 A | 11/1978 | Klaile et al. | |
| 4,153,689 A | 5/1979 | Hirai et al. | |
| 4,211,769 A | 7/1980 | Okada et al. | |
| 4,221,339 A | 9/1980 | Yoshikawa | |
| 4,249,526 A | 2/1981 | Dean et al. | |
| 4,253,468 A | 3/1981 | Lehmbeck | |
| 4,261,793 A | 4/1981 | Nakamura et al. | |
| 4,268,460 A | 5/1981 | Boiarski et al. | |
| 4,294,624 A | 10/1981 | Veltman | |
| 4,294,829 A | 10/1981 | Suzuki et al. | |
| 4,305,210 A | 12/1981 | Christensen et al. | |
| 4,338,931 A | 7/1982 | Cavazza | |
| 4,446,862 A | 5/1984 | Baum et al. | |
| 4,452,239 A | 6/1984 | Malem | |
| 4,476,804 A | 10/1984 | Glatt et al. | |
| 4,484,577 A | 11/1984 | Sackner et al. | |
| 4,486,435 A | 12/1984 | Schmidt et al. | |
| 4,503,035 A | 3/1985 | Pestka et al. | |
| 4,534,343 A | 8/1985 | Nowacki et al. | |
| 4,540,602 A | 9/1985 | Motoyama et al. | |
| 4,590,206 A | 5/1986 | Forrester et al. | |
| 4,613,500 A | 9/1986 | Suzuki et al. | |
| 4,624,251 A | 11/1986 | Miller | |
| 4,627,432 A | 12/1986 | Newell et al. | |
| 4,649,911 A | 3/1987 | Knight et al. | |
| 4,659,696 A | 4/1987 | Hirai et al. | |
| 4,698,328 A | 10/1987 | Neer et al. | |
| 4,702,799 A | 10/1987 | Tuot | |
| 4,721,709 A | 1/1988 | Seth et al. | |
| 4,739,754 A | 4/1988 | Shaner | |
| 4,748,034 A | 5/1988 | de Rham | |
| 4,748,817 A * | 6/1988 | Oura et al. ................... | 62/74 |
| 4,760,093 A | 7/1988 | Blank et al. | |
| 4,784,878 A | 11/1988 | Haak | |

(Continued)

FOREIGN PATENT DOCUMENTS

DE          3501983          7/1985

(Continued)

OTHER PUBLICATIONS

Barj et al. "Submicronic MgAl2O4 Powder Synthesis in Supercritical Ethanol." J. of Materials Sci. vol. 27. No. B p. 2187-2192 (1992).

Bjork, E. et al., "Degradable Starch Microspheres As a Nasal Delivery System for Insulin." International Journal of Pharmaceutics. 1988. Volume 47. pp. 233-238.

Bloch etal., "Dispersicns of Hydrochlorothiazide and Chlorhalidone in Pentaerythrit0l." Pharm. Acta. Helv. (1983) , 58 (1):, p. 14-22.

Bodmeier, et al., "Preparation of Biodegradable Poly(+)lactide Microparticles Using a Spray-Drying Technique", J. Pharm. Pharmocol. 1988, 40:, p. 754-757.

Bohnet. Matthias, "Calculation and Design of Gas/Solid-Injectors," Powder Tech, 1984. pp. 302-313.

(Continued)

*Primary Examiner* — Susan Tran (74) *Attorney, Agent, or Firm* — Janah & Associates, P.C.

(57) ABSTRACT

The present invention provides exemplary systems and methods for producing dry powder formulations. In one embodiment, a system (10) includes at least one conditioning zone (12) having an inlet (20) to introduce an atomized formulation (18) into the conditioning zone. A controller (14, 16) controls temperature and relative humidity of the airflow into the conditioning zone to allow amorphous-to-crystalline transformation of the atomized formulation. In another embodiment, the formulation is suspended in the conditioning zone for a residence time of sufficient duration to allow surface orientation of surface active components. A dryer (24) is coupled to the conditioning zone to dry the atomized formulation, and a collector (28) collects the formulation in powder form.

13 Claims, 6 Drawing Sheets

U.S. PATENT DOCUMENTS

| | | |
|---|---|---|
| 4,790,305 A | 12/1988 | Zoltan et al. |
| 4,794,167 A | 12/1988 | Lindner et al. |
| 4,807,814 A | 2/1989 | Douche et al. |
| 4,811,731 A | 3/1989 | Newell et al. |
| 4,818,424 A | 4/1989 | Evans et al. |
| 4,819,629 A | 4/1989 | Jonson |
| 4,823,784 A | 4/1989 | Bordoni et al. |
| 4,828,844 A | 5/1989 | Rontgen-Odenthal et al. |
| 4,833,125 A | 5/1989 | Neer et al. |
| 4,835,187 A | 5/1989 | Reuter et al. |
| 4,866,051 A | 9/1989 | Hunt et al. |
| 4,871,489 A | 10/1989 | Ketcham |
| 4,884,565 A | 12/1989 | Cocozza |
| 4,889,114 A | 12/1989 | Kladders |
| 4,907,583 A | 3/1990 | Wetterlin et al. |
| 4,926,852 A | 5/1990 | Zoltan et al. |
| 4,942,544 A | 7/1990 | McIntosh et al. |
| 4,946,828 A | 8/1990 | Markussen |
| 4,952,402 A | 8/1990 | Sparks et al. |
| 4,968,607 A | 11/1990 | Dower et al. |
| 4,984,158 A | 1/1991 | Hillsman |
| 4,995,385 A | 2/1991 | Valentini et al. |
| 5,000,888 A | 3/1991 | Kilbride, Jr. et al. |
| 5,009,367 A | 4/1991 | Nielsen |
| 5,011,678 A | 4/1991 | Wang et al. |
| 5,017,372 A | 5/1991 | Hastings |
| 5,026,550 A | 6/1991 | Aeschbach et al. |
| 5,027,806 A | 7/1991 | Zoltan et al. |
| 5,033,463 A | 7/1991 | Cocozza |
| 5,035,237 A | 7/1991 | Newell et al. |
| 5,038,769 A | 8/1991 | Krauser |
| 5,042,975 A | 8/1991 | Chien et al. |
| 5,048,514 A | 9/1991 | Ramella |
| 5,049,388 A | 9/1991 | Knight et al. |
| 5,064,501 A | 11/1991 | Boersen et al. |
| 5,066,522 A | 11/1991 | Cole et al. |
| 5,081,228 A | 1/1992 | Dower et al. |
| 5,093,316 A | 3/1992 | Lezdey et al. |
| 5,098,893 A | 3/1992 | Franks et al. |
| 5,099,833 A | 3/1992 | Michaels |
| 5,113,855 A | 5/1992 | Newhouse |
| 5,139,016 A | 8/1992 | Waser |
| 5,161,524 A | 11/1992 | Evans |
| 5,180,812 A | 1/1993 | Dower et al. |
| 5,186,164 A | 2/1993 | Raghuprasad |
| 5,200,399 A | 4/1993 | Wettlaufer et al. |
| 5,204,108 A | 4/1993 | Illum |
| 5,206,219 A | 4/1993 | Desai |
| 5,206,306 A | 4/1993 | Shen |
| 5,221,731 A | 6/1993 | Weymans et al. |
| 5,230,884 A | 7/1993 | Evans et al. |
| 5,232,707 A | 8/1993 | Lokensgard |
| 5,235,969 A | 8/1993 | Bellm |
| 5,254,330 A | 10/1993 | Ganderton et al. |
| 5,260,306 A | 11/1993 | Boardman et al. |
| 5,269,980 A | 12/1993 | Levendis et al. |
| 5,279,708 A | 1/1994 | Wood et al. |
| 5,290,765 A | 3/1994 | Wettlaufer et al. |
| 5,295,479 A | 3/1994 | Lankinen |
| 5,302,581 A | 4/1994 | Sarin et al. |
| 5,309,900 A | 5/1994 | Knoch et al. |
| 5,320,094 A | 6/1994 | Laube et al. |
| 5,320,714 A | 6/1994 | Brendel |
| 5,331,953 A | 7/1994 | Andersson et al. |
| 5,354,562 A | 10/1994 | Platz et al. |
| 5,354,934 A | 10/1994 | Pitt et al. |
| 5,356,636 A | 10/1994 | Schneider et al. |
| 5,364,838 A | 11/1994 | Rubsamen |
| 5,376,359 A | 12/1994 | Johnson |
| 5,376,386 A | 12/1994 | Ganderton et al. |
| 5,384,133 A | 1/1995 | Boyes et al. |
| 5,458,135 A | 10/1995 | Patton et al. |
| 5,482,927 A | 1/1996 | Maniar et al. |
| 5,487,378 A | 1/1996 | Robertson et al. |
| 5,487,916 A * | 1/1996 | Christensen .................. 427/213 |
| 5,506,203 A | 4/1996 | Backstrom et al. |
| 5,518,709 A | 5/1996 | Sutton et al. |
| 5,518,998 A | 5/1996 | Backstrom et al. |
| 5,580,856 A | 12/1996 | Prestrelski et al. |
| 5,607,697 A | 3/1997 | Alkire et al. |
| 5,622,657 A | 4/1997 | Takada et al. |
| 5,624,530 A | 4/1997 | Sadykhov et al. |
| 5,628,937 A | 5/1997 | Oliver et al. |
| 5,648,096 A | 7/1997 | Gander et al. |
| 5,651,990 A | 7/1997 | Takada et al. |
| 5,667,806 A | 9/1997 | Kantor |
| 5,687,905 A | 11/1997 | Tsai |
| 5,707,644 A | 1/1998 | Illum |
| 5,716,558 A | 2/1998 | Nielsen et al. |
| 5,723,269 A | 3/1998 | Akagi et al. |
| 5,741,478 A | 4/1998 | Osborne et al. |
| 5,776,491 A | 7/1998 | Allen, Jr. et al. |
| 5,800,598 A | 9/1998 | Chein et al. |
| 5,807,576 A | 9/1998 | Allen, Jr. et al. |
| 5,855,913 A | 1/1999 | Hanes et al. |
| 5,874,029 A | 2/1999 | Subramaniam et al. |
| 5,874,064 A | 2/1999 | Edwards et al. |
| 5,922,253 A | 7/1999 | Herbert et al. |
| 5,924,216 A | 7/1999 | Takahashi |
| 5,964,416 A | 10/1999 | Jaeger et al. |
| 5,970,974 A | 10/1999 | Van Der Linden et al. |
| 5,976,574 A | 11/1999 | Gordon |
| 5,981,474 A | 11/1999 | Manning et al. |
| 5,985,248 A | 11/1999 | Gordon et al. |
| 5,985,309 A | 11/1999 | Edwards et al. |
| 5,993,805 A | 11/1999 | Sutton et al. |
| 5,997,848 A | 12/1999 | Patton et al. |
| 6,001,336 A | 12/1999 | Gordon |
| 6,015,546 A | 1/2000 | Sutton et al. |
| 6,017,310 A | 1/2000 | Johnson et al. |
| 6,022,525 A | 2/2000 | Sutton et al. |
| 6,051,256 A | 4/2000 | Platz et al. |
| 6,051,257 A | 4/2000 | Kodas et al. |
| 6,077,543 A | 6/2000 | Gordon et al. |
| 6,080,721 A | 6/2000 | Patton |
| 6,117,455 A | 9/2000 | Takada et al. |
| 6,123,924 A | 9/2000 | Mistry et al. |
| 6,136,295 A | 10/2000 | Edwards et al. |
| 6,149,941 A | 11/2000 | Schwarz et al. |
| 6,153,129 A | 11/2000 | Herbert et al. |
| 6,156,511 A | 12/2000 | Schatz et al. |
| 6,165,511 A | 12/2000 | Schwarz et al. |
| 6,174,469 B1 | 1/2001 | Ganan-Calvo |
| 6,197,835 B1 | 3/2001 | Ganan-Calvo |
| 6,223,455 B1 | 5/2001 | Chickering, III et al. |
| 6,258,341 B1 | 7/2001 | Foster et al. |
| 6,290,991 B1 | 9/2001 | Roser et al. |
| 6,308,434 B1 | 10/2001 | Chickering, III et al. |
| 6,315,983 B1 | 11/2001 | Eistetter |
| 6,316,029 B1 | 11/2001 | Jain et al. |
| 6,331,290 B1 | 12/2001 | Morgan |
| 6,331,310 B1 | 12/2001 | Roser et al. |
| 6,365,190 B1 | 4/2002 | Gordon et al. |
| 6,372,258 B1 | 4/2002 | Platz et al. |
| 6,383,810 B2 | 5/2002 | Fike et al. |
| 6,416,739 B1 | 7/2002 | Rogerson et al. |
| 6,423,344 B1 | 7/2002 | Platz et al. |
| 6,451,349 B1 | 9/2002 | Robinson et al. |
| 6,455,028 B1 | 9/2002 | Wulffhart et al. |
| 6,503,480 B1 | 1/2003 | Edwards et al. |
| 6,560,897 B2 | 5/2003 | Chickering, III et al. |
| 6,565,885 B1 | 5/2003 | Tarara et al. |
| 6,572,893 B2 | 6/2003 | Gordon et al. |
| 6,582,728 B1 | 6/2003 | Platz et al. |
| 6,592,904 B2 | 7/2003 | Platz et al. |
| 6,656,492 B2 | 12/2003 | Kajiyama et al. |
| 2002/0071871 A1 | 6/2002 | Snyder et al. |
| 2002/0081266 A1 | 6/2002 | Woolfe et al. |
| 2002/0175225 A1 | 11/2002 | Boersen et al. |
| 2003/0124193 A1 | 7/2003 | Snyder et al. |
| 2003/0203036 A1 | 10/2003 | Gordon et al. |
| 2003/0215514 A1 | 11/2003 | Platz et al. |

FOREIGN PATENT DOCUMENTS

| | | |
|---|---|---|
| DE | 3806537 | 9/1989 |
| DE | 4329204 | 3/1995 |
| EP | 0002018 | 5/1979 |

| | | |
|---|---|---|
| EP | 0072046 | 2/1983 |
| EP | 0122036 | 10/1984 |
| EP | 0237507 | 9/1987 |
| EP | 0260971 | 3/1988 |
| EP | 0344375 | 12/1989 |
| EP | 0347779 | 12/1989 |
| EP | 0360340 | 3/1990 |
| EP | 0383569 | 8/1990 |
| EP | 0408801 | 1/1991 |
| EP | 0461930 | 12/1991 |
| EP | 0467172 | 1/1992 |
| EP | 0468914 | 1/1992 |
| EP | 469725 | 2/1992 |
| EP | 0492797 | 6/1992 |
| EP | 0506293 | 9/1992 |
| EP | 512693 | 11/1992 |
| EP | 0535937 | 4/1993 |
| EP | 0580428 | 1/1994 |
| EP | 0611567 | 8/1994 |
| EP | 628331 | 12/1994 |
| EP | 0655237 | 5/1995 |
| EP | 674541 | 10/1995 |
| EP | 0677332 | 10/1995 |
| EP | 681843 | 11/1995 |
| EP | 709085 | 5/1996 |
| EP | 972526 | 1/2000 |
| EP | 1004349 | 5/2000 |
| FR | 2257351 | 8/1975 |
| GB | 473471 | 10/1937 |
| GB | 621785 | 4/1949 |
| GB | 1112553 | 5/1968 |
| GB | 1527605 | 8/1975 |
| GB | 2105189 | 3/1983 |
| JP | 55-167218 | 12/1980 |
| JP | 05-194200 | 3/1993 |
| JP | 06-293636 | 10/1994 |
| JP | 07-187996 | 7/1995 |
| JP | 08-505152 | 6/1996 |
| JP | 2000-510471 | 8/2000 |
| NL | 7712041 | 5/1979 |
| SU | 0628930 | 10/1978 |
| SU | 1003926 | 1/1979 |
| WO | WO97/26863 | 7/1931 |
| WO | WO88/04556 | 6/1988 |
| WO | WO88/07870 | 10/1988 |
| WO | WO88/09163 | 12/1988 |
| WO | WO90/07351 | 7/1990 |
| WO | WO90/09780 | 9/1990 |
| WO | WO90/11139 | 10/1990 |
| WO | WO90/15635 | 12/1990 |
| WO | WO91/02545 | 3/1991 |
| WO | WO91/02558 | 3/1991 |
| WO | WO91/16882 | 11/1991 |
| WO | WO92/18164 | 10/1992 |
| WO | WO93/07465 | 4/1993 |
| WO | WO93/09832 | 5/1993 |
| WO | WO96/32096 | 10/1993 |
| WO | WO93/25198 | 12/1993 |
| WO | WO94/08552 | 4/1994 |
| WO | WO94/08627 | 4/1994 |
| WO | WO94/15636 | 7/1994 |
| WO | WO95/00127 | 1/1995 |
| WO | WO95/00128 | 1/1995 |
| WO | WO95/08987 | 4/1995 |
| WO | WO95/23613 | 9/1995 |
| WO | WO95/24183 | 9/1995 |
| WO | WO95/31479 | 11/1995 |
| WO | WO96/03978 | 2/1996 |
| WO | WO96/05809 | 2/1996 |
| WO | WO96/09814 | 4/1996 |
| WO | WO96/11580 | 4/1996 |
| WO | WO96/15814 | 5/1996 |
| WO | WO96/32149 | 10/1996 |
| WO | WO96/40076 | 12/1996 |
| WO | WO97/03649 | 2/1997 |
| WO | WO97/28788 | 8/1997 |
| WO | WO97/36574 | 10/1997 |
| WO | WO97/36578 | 10/1997 |
| WO | WO97/41833 | 11/1997 |
| WO | WO97/44067 | 11/1997 |
| WO | WO98/01228 | 1/1998 |
| WO | WO95/13864 | 5/1998 |
| WO | WO98/29096 | 7/1998 |
| WO | WO98/29098 | 7/1998 |
| WO | WO98/31346 | 7/1998 |
| WO | WO98/36888 | 8/1998 |
| WO | WO98/47493 | 10/1998 |
| WO | WO99/16419 | 4/1999 |
| WO | WO99/16422 | 4/1999 |
| WO | WO99/17742 | 4/1999 |
| WO | WO99/30834 | 6/1999 |
| WO | WO99/31019 | 6/1999 |
| WO | WO99/32083 | 7/1999 |
| WO | WO99/61006 | 12/1999 |
| WO | WO99/64014 | 12/1999 |
| WO | WO00/00176 | 1/2000 |
| WO | WO00/09084 | 2/2000 |
| WO | WO00/10541 | 3/2000 |
| WO | WO00/12278 | 3/2000 |
| WO | WO00/13668 | 3/2000 |
| WO | WO00/66256 | 11/2000 |
| WO | WO00/76673 | 12/2000 |
| WO | WO01/03673 | 1/2001 |
| WO | WO01/13885 | 3/2001 |
| WO | WO01/15664 | 3/2001 |
| WO | WO01/45731 | 6/2001 |
| WO | WO01/49263 | 7/2001 |
| WO | WO01/64188 | 9/2001 |
| WO | WO01/87278 | 11/2001 |
| WO | WO02/09669 | 2/2002 |
| WO | WO02/15876 | 2/2002 |
| WO | WO02/15880 | 2/2002 |
| WO | WO02/078675 | 10/2002 |
| WO | WO03/000202 | 1/2003 |

OTHER PUBLICATIONS

Brandenberger, "A New Multinozzle Encapsulation/Immobilisation System to Produce Uniform Beads of Alginate", Journal of Biotechnology, vol. 63, No. 1, p. 73-80 (1998).

Budrik, G. K. et al.. "Ejector Feeders for Pneumatic Transport Systems," Chemical Petroleum Engineering. Sep.-Oct. 1978. vol. 14, Nos. 9-10. pp. 9-10.

Byron, P. R. et al. "Drug Delivery Via the Respiratory Tract," Journal or Aerosol Medicine, 1994. vol. 7, No. 1. pp. 49-75.

Carpenter, John F. et al., "Modes of Stabilization of a Protein by Organic Solutes During Desiccation," Cryobiology. 1988. vol. 25, pp. 459-470.

Chien, Y. W. et al.. "Intranasal Drug Delivery for Systemic Medications," Critical Reviews in Therapeutic Drug Carries Systems. 1987, vol. 4, Issue 2, pp. 67-92. (1 page).

Colthorpe P. et al., "The pharmacokinetics of pulmonary-delivered insulin: a comparison of intratrachaal and aerosol administration to the rabbit.," Pharmaceutical Research. 1992. vol. 9. No. 6, pp. 764-768. (1 page).

de Boer, et al., "Air classifier technology (ACT) in dry powder inhalation Part 2. The effect of lactose carrier surface properties on the drug-to-carrier interaction in adhesive mixtures for inhalation", International Journal of Pharmaceutics, vol. 260, 2003, Elsevier Science B.V., pp. 201-216.

Duchateau. G. etal . Bile Salts and Intranasal Drug Absorption/" International Journal of Pharmaceutics, 1986. vol. 31. pp. 193-199.

Elliott, et: al . "Parenteral Absorption of insulin From the Lung in Diabetic Children." Aust.Paediatr. J. 1987, vol. 23. pp. 293-297.

EP Search Report dated Dec. 16, 2005 for Application No. 97926420.7.

EPO Communication dated May 15, 2007 for European Application No. 02776395.2.

EPO Communication dated Nov. 2, 2006 for European Application No. 97926420.7.

European Communication, Application No. 97 954 240.4, mail date Jul. 31, 2008.

Examiner's Report for Slovak Republic Patent Application No. PP 0146-2006-2001.

Ferrari, et al., "The Surface Roughness of Lactose Particles Can Be Modulated by Wet-Smoothing Using a High-Shear Mixer", AAPS PharmSciTech, Dec. 2004, vol. 5, No. 4, Article 60, (http://www.aapspharmscitech.org), pp. 1-6.

Fox, etal., "Performance of a Venturi Eductor as a Feeder in a Pneumatic Conveying System." Powder & Bulk Engineering, Mar. 1988. pp. 33-36.

Friedman. T., "Progress Toward Human Gene Therapy," Science, Jun. 16, 1989, vol. 244, pp. 1275-1281.

Govinda Rao, A. R., "Aerosol insulin inhalation Enquiry," Indian J. Physiol Pharmacol, 1959. vol. 3, pp. 161-167.

Habener. Joel F., "Parathyroid Homione: Secretion and Metabolism in Vivo," Proc. Nat. Acad. Sci. USA. Dec. 1971. vol. 68. No. 12. pp. 2986-2991.

Hastings, et al., "Clearance of Different-Sized Proteins from the Alveolar Space in Humans and Rabbits," J.Appl. Physiol., 1192, vol. 73, pp. 1310-1316. (1 page).

Hesch, R. D., Pulsatile secretion of parathyroid hormone and its action on a type I and type II PTH receptor: a hypothesis for understanding osteoporosis} Calcihed Tissue int. 1988, vol. 42. pp. 341-344.

Hino et al., "Development of a new type nozzle and spray-drier for industrial production of line powders", European J. of Pharmaceutics and Biopharmaceutics (2000), vol. 49, pp. 79-85.

Hubbard, Richard C. and Ronald G. Cryscal, "Abstract Strategies for aerosol therapy of alpha 1-antitrypsin deficiency by the aerosol route.." Lung. 1990, vol.168, Supplement: 1990, Proceedings ofthe 8th Congress of SEP. Edited by H. Matthys, pp. 565-578.

Laube. Beth L. et al., "Preliminary study of the efficacy of insulin aerosol delivered by oral inhalation in diabetic patients." JAMA. Apr. 28, 1993, vol. 269. No. 16. pp. 2106-2109. (1 page).

Lee, Shih-Wei etal., "Development of an aerosol dosage form containing insulin," Journal of Pharmaceutical Sciences. vol. 65, No. 4, Apr. 1976, pp. 567-572. (1 page).

Liu, Fang-Yu et al., "Pulmonary Delivery of Free and Liposomal Insulin," Pharmaceutical Research 1993, vol. 10. No. 2. pp. 228-232.

Masters, "The Process Stages of Spray Drying: Atomization", Spray Drying Handbook, pp. 230-247.

Moses, Diabetes, vol. 32, Nov. 1983, pp. 1040-1047.

Mumenthaler et al., "Feasibility Study on Spray-Drying Protein Pharmaceuticals: Recombinant Human Growth Hormone and Tissue-Type Plasminogen Activator.", Pharm. Res. (1994), 11(1), p. 12-20.

Nagai, Tsuneji et al., "Powder Dosage Form of Insulin for Nasal Administration," Journal of Controlled Release. 1984. vol. 1, pp. 15-22.

Neer, 2. M. et al.."The Use of Parathyroid Hormone Plus 1.25-Dihydroxyvitamin D to increase Trabecular Bone in Osteoporotic Men and Poscmenopausal Women," Osteoporosis. 1987, vol. 53. pp. 829-835.

Nieminen, M. M. etal., "Aerosol Deposition in Automatic Dosimeter NebUlization." Eur. J. Resir. Dis. 1987, vol. 71. PC. 145>>52. (1 page) Partial EP Search Report dated Jan. 4, 2006 for Application No. 97926420.7.

Office Action in European Application No. 08 16 0325.

Patton, John S. et al., "(D) Routes of Delivery: Case Studies—(2) Pulmonary Delivery of Peptides and Proteins for Systemic Action," Advanced Drug Delivery Reviews. 1992. vol. 8, pp. 179-196.

Pikal, Michael et al., "Moisture Transfer From Stopper to Product and Resulting.Stability Implications," Develooments in Bioloaical Standardardization. 1991., vol. 74, International Symposium on Biological Product Freeze-Drying and Formulation, pp. 1.

Pikal, Michael J., "Polymorphisms in Pharmaceutical Solids," AAPS. Nov. 5, 1992. Annual Meeting and Expositions, San Antonio, TX. 2 pages.

Pittman, et al., "Pneumatic Conveying of Bulk Solids Using a Vacuum Aerated Feed Nozzle." Solid Handling Conference Paper C4. Jun. 10-12, 1985 Thames Polytechnic London, United Kingdom, pp. C41-CS1.

Prusse, et al., "Production of Spherical Beads by Jet Cutting", 23 ed, vol. 12, Chem. Eng. Technol. (2000).

Rosenfeld, et al., "Adenovirus-Mediated Transfer of a Recombinant a- 1- Antitrypsin Gene to the Lung Epithelium in Vivo," Science. vol. 252, Apr. 19, 1991. pp. 431-434.

Rote Liste 1996, abstract 24-301: Exosurf® Neonatal.

Ryden, Lena et al., "Effect of -Polymers and Microspheres on the Nasal Absorption of Insulin in Rats," International Journal of Pharmaceutics. 1992, vol. 83, pp. 1-10.

Sakr, Farouk M., "A New Approach for Insulin Delivery Via the Pulmonary Route: Design and Pharmacokinetics in Non-Diabetic Rabbits," International Journal of Pharmaceutics. 1992, vol. 86, pp. 1-7. (1 page).

Schluter, Klaus J. et al., "Pulmonary Administration of Human insulin in Volunteers and Type I-Diabetics," Abstract Reproduction Form for Annual Meeting Program Published in Diabetes Feb. 1, 1984. one page.

Stribling et: al., "The Mouse As a Model for Cationic Liposome-Based, Aerosolized Gene Delivery," Journal of Biopharmaceutical Sciences. 1992, 3(1./2), pp. 255-263.

Taylor, et al., "Liposomes for Drug Delivery to the Respiratory Tract", Drug Development and Industrial Pharmacy 1993, 19(1&2), p. 124-142.

Underwood, et al., "A Novel Technique for the Administration of Bronchodilator Drugs Formulated As Dry Powders to the Anaesthetized Guinea Pig," Journal of Pharmacological Methods. 1991. vol. 26. pp. 203-210.

Wigley, Frederick et al., "Insulin Across Respiratory Mucosae by Aerosol Delivery," Diabetes. 1971, vol. 20, No. 8, pp. 552-556. (1 page).

Witham, Clyde L., "Dry Dispersion With Sonic Velocity Nozzles," Workshop on Dissemination Techniques for Smoke and Obscurants Chemical Systems Laboratory. Aberdeen Proving Group. MD, Mar. 14-16, 1983, pp. 1-26.
Yoshida, H., "Absoition of Insulin Delivered to Rabbit Trachea Using Aerosol Dosage F□rm," Journal of Pharmaceutical Sciences. May 1979, vol. 68, No. 5, pp. 670671. (1 page).

* cited by examiner

```
                    ┌──────────────────┐
                    │  ATOMIZE SOLUTION │ ─── 102
                    └──────────────────┘
                             │
┌──────────────┐   ┌──────────────────────┐   ┌──────────────┐
│ (OPTIONALLY) │   │ INTRODUCE ATOMIZED   │   │  CONTROL     │
│  ADD HUMID   │──▶│  SOLUTION TO         │◀──│  TEMP OF     │
│     AIR      │   │  CONDITIONING ZONE   │   │ CONDITIONING │
└──────────────┘   └──────────────────────┘   │    ZONE      │
    108                    104                └──────────────┘
                             │                       106
                             ▼
              ┌──────────────────────────────┐
              │ SUSPEND FORMULATION IN       │
              │ CONDITIONING ZONE FOR A      │
              │ RESIDENCE PERIOD TO          │
              │ FACILITATE MOVEMENT          │─── 110
              │ OF SURFACE ACTIVE            │
              │ MOLECULES TO                 │
              │ DROPLET SURFACES             │
              └──────────────────────────────┘
                             │
                             ▼
                    ┌──────────────────┐
                    │  DRY FORMULATION │ ─── 112
                    └──────────────────┘
                             │
                             ▼
                    ┌──────────────────┐
                    │ COLLECT DRY POWDER│ ─── 114
                    └──────────────────┘
```

SPRAY DRYING PROCESS CONTROL OF DRYING KINETICS

CROSS-REFERENCE TO RELATED APPLICATIONS

This is a continuation of application Ser. No. 09/733,269 filed on Dec. 8, 2000 now U.S. Pat. No. 7,575,761, which is a continuation-in-part of application Ser. No. 09/607,975 filed on Jun. 30, 2000 now abandoned, the entire disclosures of which are hereby incorporated by reference.

FIELD OF THE INVENTION

The present invention relates generally to systems and methods for manufacturing dry powder formulations. More specifically, the present invention provides systems and methods for the production of spray dried powders suitable for pharmaceutical applications, preferably for dry powders to be administered by inhalation. According to the invention, the drying kinetics of a spray drying process may be controlled, for example, to facilitate surface diffusion of surface active components or to facilitate amorphous-to-crystalline transformations during the manufacture of dry powder formulations.

BACKGROUND OF THE INVENTION

Over the years, certain drugs have been sold in compositions suitable for pulmonary delivery to treat various conditions in humans. Such pulmonary drug delivery compositions include an aerosolized drug formulation that is inhaled by the patient so that the active agent can reach the alveolar region of the lungs.

Pulmonary drug delivery can be achieved by, for example, delivery of dry powder formulations to the deep lung. These powders have been prepared by spray drying as described in WO 96/32149, WO 99/16419 and U.S. Pat. Nos. 5,976,574, 5,985,248, 6,001,336, and 6,051,256, the disclosures of which are incorporated herein in their entirety. Preparing pharmaceutical compositions as stable dry powders by spray drying, however, poses many challenges. In order to scale up the spray drying process, it is desirable to increase the total solids content of the feed stream. It was found, however, that the emitted dose of powders prepared from higher total solids content feed streams, that is above about 1% (w/v), declined significantly.

In addition, the ability to deliver pharmaceutical compositions as dry powders poses many challenges. For example, particles containing both crystalline and amorphous phases may exhibit physical or chemical instability. Transformations of the materials during storage from amorphous to crystalline may result in such instability as a result of particle fusion and other physical changes. Further, crystallization tends to increase the water content in the remaining amorphous phase and thereby decrease the glass transition temperature ($T_g$) of the materials. Increased water content of the amorphous region increases molecular mobility and may increase chemical degradation reaction rates (i.e., hydrolysis, aggregation, etc.). Formulations having a higher percentage of crystallinity are less likely to degrade during storage.

It is known to provide spray dryers with drying zones which are maintained at different temperatures in order to provide some control of the drying kinetics. For example, U.S. Pat. No. 4,257,799 discloses a method for producing small hollow glass spheres having an outer diameter from about 100 to 500 microns wherein the method involves introducing aqueous droplets of a glass-forming solution into a long vertical drop oven or furnace having varying temperature regions.

U.S. Pat. Nos. 5,632,100, 5,924,216 and 4,281,024 also disclose spray drying with multiple drying zones, in which larger particles are typically subjected to a secondary drying in order to achieve desired moisture content.

U.S. Pat. No. 6,051,257 discloses structurally modifying particles after they are formed by a spray drying process in order to impart desired physical properties to the particles. The particle modifier is typically a furnace having temperature control independent of the spray dryer furnace and is positioned to receive the formed particles after they exit the spray dryer furnace.

U.S. Pat. No. 5,874,063 to Briggner et al. describes a method for increasing the crystallinity of conventional fine particles by treating the already manufactured fine particles with a solvent in the vapor phase and then removing the excess solvent. The solvent may be an organic solvent or it may be water.

WO 00/64552 discloses a method of spray drying and a plant therefore whereby spray drying is performed at increased pressure. The invention is directed to spray drying where an amorphous product is desired and/or where a high bulk density powder is desired. Spray drying according to this disclosure is conducted in a pressurized environment not below 1.25 bar absolute.

There remains a need to provide control of drying kinetics of spray drying processes in order to produce particles of desired physical properties for pharmaceutical applications such as the preparation of dry powders for inhalation. It is desirable to provide systems and methods which provide for dry powders with acceptable pulmonary delivery characteristics. The present invention overcomes the above shortcomings in the prior art.

SUMMARY OF THE INVENTION

The present invention provides exemplary systems and methods for producing dry powder formulations which in one aspect encourage surface diffusion of surface active components during the formation of dry powder medicaments, and therefore have improved emitted doses for pulmonary delivery. In another aspect of this invention, we have found that it is possible to provide improved control of the drying kinetics of spray drying methods in order to encourage amorphous-to-crystalline transformations during drying without exposing the finished fine particles to added water, solvent or thermal processing. We are thus able to reduce or minimize the potential instability of a fine particle formulation throughout its shelf life.

One embodiment of the present invention is directed to spray drying of pharmaceutical formulations containing surface active components. A system is provided for producing dry powders wherein the system includes an atomizer and at least one conditioning zone coupled to the atomizer to suspend an atomized formulation for a residence time where the atomized formulation remains in the liquid state. A dryer is coupled to the conditioning zone to dry the formulation exiting the conditioning zone. Further, a collector collects the dried formulation in powder form. In this manner, by controlling the residence time, temperature and relative humidity in the conditioning zone, the atomized formulation is suspended in a manner which allows the droplets to reach thermodynamic equilibrium, wherein the surface active component diffuses to the surface of the droplets to reach its equilibrium orientation. According to this aspect of the invention, the temperature and relative humidity in the conditioning zone is maintained at levels to minimize droplet drying in the conditioning zone during the period immediately following atomization, preferably at levels which prevent solvent evaporation all together.

The present invention further provides methods for producing a powdered formulation having a high concentration of surface active components on the surface of the particles.

In one method of the present invention, an atomized formulation of liquid droplets is introduced into a conditioning zone. The atomized formulation is suspended within the conditioning zone for a residence time, during which the formulation remains in the liquid state to allow the droplets to reach thermodynamic equilibrium and allow diffusion of surface active components to the surface of the droplets. The method includes transferring the conditioned formulation to a dryer, introducing a heated gas into the drier to dry the conditioned formulation and form dry particles, and collecting the dry particles.

In another aspect, the present invention provides exemplary systems and methods for producing dry powder formulations which encourage amorphous-to-crystalline transformations of such formulations during manufacture to result in increased stability during storage. The present invention is based at least in part on the unexpected observation that storage stability of powdered formulations is greatly effected by the manufacturing conditions of the powders. According to this aspect of the invention, a multi-zonal spray dryer system and method of use are provided for producing dry powders. The system includes at least one conditioning zone having an inlet to introduce an atomized formulation into the conditioning zone. Air flow into the conditioning zone is controlled to control temperature and relative humidity.

The atomized formulation remains in the conditioning zone for a residence time at a predetermined temperature and relative humidity to allow equilibration of the water activity in the atomized droplet with the environment of the conditioning zone. This equilibration of water activity, or water content, results in partial drying of the droplet and promotes amorphous-to-crystalline transformations in the atomized formulation. A dryer is coupled to the conditioning zone to dry the atomized formulation into the final dried particles. Further, a collector collects the dried particles. In this manner, by controlling temperature and relative humidity in the conditioning zone and by controlling the residence time, the atomized formulation is conditioned and dried in a manner that promotes amorphous-to-crystalline transformation. According to this aspect of the invention, partially dried particles leave the conditioning zone wherein the particles retain a sufficiently high moisture content so as to require further drying. This excess moisture in the partially dried particles acts as a plasticizer to allow crystallization. The partially dried particles are then exposed to temperatures and relative humidity levels that allow crystallization to occur at a rate to convert amorphous material within a residence time of a few seconds.

According to another aspect of the invention, the pressure is controlled in order to provide elevated pressures of up to 75 atmospheres within the conditioning zones and/or within the dryer.

DETAILED DESCRIPTION OF THE INVENTION

Definitions

"Active agent" as described herein includes an agent, drug, compound, composition of matter or mixture thereof which provides some pharmacologic, often beneficial, effect. This includes feeds, feed supplements, nutrients, drugs, vaccines, vitamins, and other beneficial agents. As used herein, the terms further include any physiologically or pharmacologically active substance that produces a localized or systemic effect in a patient. The active agent that can be delivered includes antibiotics, antiviral agents, anepileptics, analgesics, anti-inflammatory agents and bronchodilators, and viruses and may be inorganic and organic compounds, including, without limitation, drugs which act on the peripheral nerves, adrenergic receptors, cholinergic receptors, the skeletal muscles, the cardiovascular system, smooth muscles, the blood circulatory system, synaptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, polysaccharides, steroids, hypnotics and sedatives, psychic energizers, tranquilizers, anticonvulsants, muscle relaxants, antiparkinson agents, analgesics, anti-inflammatories, muscle contractants, antimicrobials, antimalarials, hormonal agents including contraceptives, sympathomimetics, polypeptides, and proteins capable of eliciting physiological effects, diuretics, lipid regulating agents, antiandrogenic agents, antiparasitics, neoplastics, antineoplastics, hypoglycemics, nutritional agents and supplements, growth supplements, fats, antienteritis agents, electrolytes, vaccines and diagnostic agents.

Examples of active agents useful in this invention include but are not limited to insulin, calcitonin, erythropoietin (EPO), Factor VIII, Factor IX, ceredase, cerezyme, cyclosporine, granulocyte colony stimulating factor (GCSF), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-2, luteinizing hormone releasing hormone (LHRH), somatostatin, somatostatin analogs including octreotide, vasopressin analog, follicle stimulating hormone (FSH), insulin-like growth factor, insulintropin, interleukin-1 receptor antagonist, interleukin-3, interleukin-4, interleukin-6, macrophage colony stimulating factor (M-CSF), nerve growth factor, parathyroid hormone (PTH), thymosin alpha 1, IIb/IIIa inhibitor, alpha-1 antitrypsin, respiratory syncytial virus antibody, cystic fibrosis transmembrane regulator (CFTR) gene, deoxyribonuclease (Dnase), bactericidal/permeability increasing protein (BPI), anti-CMV antibody, interleukin-1 receptor, 13-cis retinoic acid, pentamidine isethionate, natural or synthetic lung surfactant, nicotine, albuterol sulfate, metaproterenol sulfate, beclomethasone dipropionate, triamcinolone acetamide, budesonide acetonide, ipratropium bromide, flunisolide, fluticasone, cromolyn sodium, ergotamine tartrate and the analogues, agonists and antagonists of the above, ciprofloxacin, tobramicin, gentamicin, and azithromicycin. Active agents may further comprise nucleic acids, present as bare nucleic acid molecules, viral vectors, associated viral particles, nucleic acids associated or incorporated within lipids or a lipid-containing material, plasmid DNA or RNA or other nucleic acid construction of a type suitable for transfection or transformation of cells, particularly cells of the alveolar regions of the lungs. The active agents may be in various forms, such as soluble and insoluble charged or uncharged molecules, components of molecular complexes or pharmacologically acceptable salts. The active agents may be naturally occurring molecules or they may be recombinantly produced, or they may be analogs of the naturally occurring or recombinantly produced active agents with one or more amino acids added or deleted. Further, the active agent may comprise live attenuated or killed viruses suitable for use as vaccines.

The active agent of the present invention may optionally be combined with pharmaceutical carriers or excipients which are suitable for respiratory and pulmonary administration. Such carriers or excipients may serve simply as bulking agents when it is desired to reduce the active agent concentration in the powder which is being delivered to a patient, or may be added to the active agent prior to processing to improve the stability and/or dispersability of the powder within a powder dispersion device. In other embodiments, the excipients may be delivered via the pulmonary route without an active agent, for example in clinical trials as a placebo. Such excipients include but are not limited to (a) carbohydrates, e.g., monosaccharides such as fructose, galactose, glucose, D-mannose, sorbose, and the like; disaccharides, such as lactose, trehalose, cellobiose, and the like; cyclodextrins, such as 2-hydroxypropyl-β-cyclodextrin; and polysaccharides, such as raffinose, maltodextrins, dextrans, and the like; (b) amino acids, such as glycine, arginine, aspartic acid, glutamic acid, cysteine, lysine, and the like; (c) organic salts prepared from organic acids and bases, such as sodium citrate, sodium ascorbate, magnesium gluconate, sodium gluconate, tromethamin hydrochloride, and the like; (d) peptides and proteins such as aspartame, human serum albumin, gelatin, and the like; and (e) alditols, such as mannitol, xylitol, and the like. A preferred group of carriers includes lactose, trehalose, raffinose, maltodextrins, glycine, sodium citrate, human serum albumin and mannitol.

"Dry powder" refers to a composition that consists of finely dispersed solid particles that are free flowing and capable of (i) being readily dispersed in an inhalation device and (ii) inhaled by a subject so that a portion of the particles reach the lungs to permit penetration into the alveoli. Such a powder is considered to by "respirable" or suitable for pulmonary delivery. The term dry, in reference to the powder, means that the composition has a moisture content which allows the particles to be readily dispersed in an inhalation device to form an aerosol. A dry powder will typically contain less than about 10 percent moisture, preferably less than 5% moisture, and more preferably will contain less than about 3 percent moisture.

"Emitted dose" or "ED" refers to an indication of the delivery of dry powder from a suitable a suitable inhaler device after a firing or dispersion event from a powder unit or reservoir. ED is defined as the ratio of the delivered dose to the nominal dose (i.e. the mass of the powder per unit dose placed into a suitable inhaler device prior to firing). The ED is an experimentally-determined amount, and is typically determined using an in-vitro device set up which mimics patient dosing. To determine an ED value, a nominal dose of dry powder (as defined above) is placed into a suitable inhaler device, which is then actuated, dispersing the powder. The resulting aerosol cloud is then drawn by vacuum from the device, where it is captured on a tared filter attached to the device mouthpiece. The amount of powder that reaches the filter constitutes the delivered dose. For example, for a 5 mg, dry powder-containing blister pack placed into an inhalation device, if dispersion of the powder results in the recovery of 4 mg powder on a tared filter as described above, then the ED for the dry powder composition is 4 mg (delivered dose)/5 mg (nominal dose)=80%.

"Mass median diameter" or "MMD" is a measure of median particle size, since the powders of the invention are generally polydisperse (i.e., consist of a range of particle sizes). MMD values as reported herein are determined by centrifugal sedimentation, although any number of commonly employed techniques can be used for measuring median particle size.

"Mass median aerodynamic diameter" or "MMAD" is a measure of the aerodynamic size of a dispersed particle. The aerodynamic diameter is used to describe an aerosolized powder in terms of its settling behavior, and is the diameter of a unit density sphere having the same settling velocity, generally in air, as the particle. The aerodynamic diameter encompasses particle shape, density and physical size of a particle. As used herein, MMAD refers to the midpoint or median of the aerodynamic particle size distribution of an aerosolized powder determined by cascade impaction.

"Powdered formulation" means the active agent as defined above in a formulation that is suitable for pulmonary delivery or the excipient that is suitable for pulmonary delivery or a combination of the active agent and the excipient. The powdered formulation may be delivered in the dry powder form or it may be in a mixture with a suitable low boiling point, highly volatile propellant. It is to be understood that more than one active agent or excipient may be incorporated into the powdered formulation and that the use of the term "agent" or "excipient" in no way excludes the use of two or more such agents or excipients.

"Surface active components" refers to any component of a formulation used with the systems and methods of the present invention which acts to decrease the surface tension of the droplets and may be the active agent including surface active proteins such as insulin, or may be an excipient added to the formulation.

Figure 1:
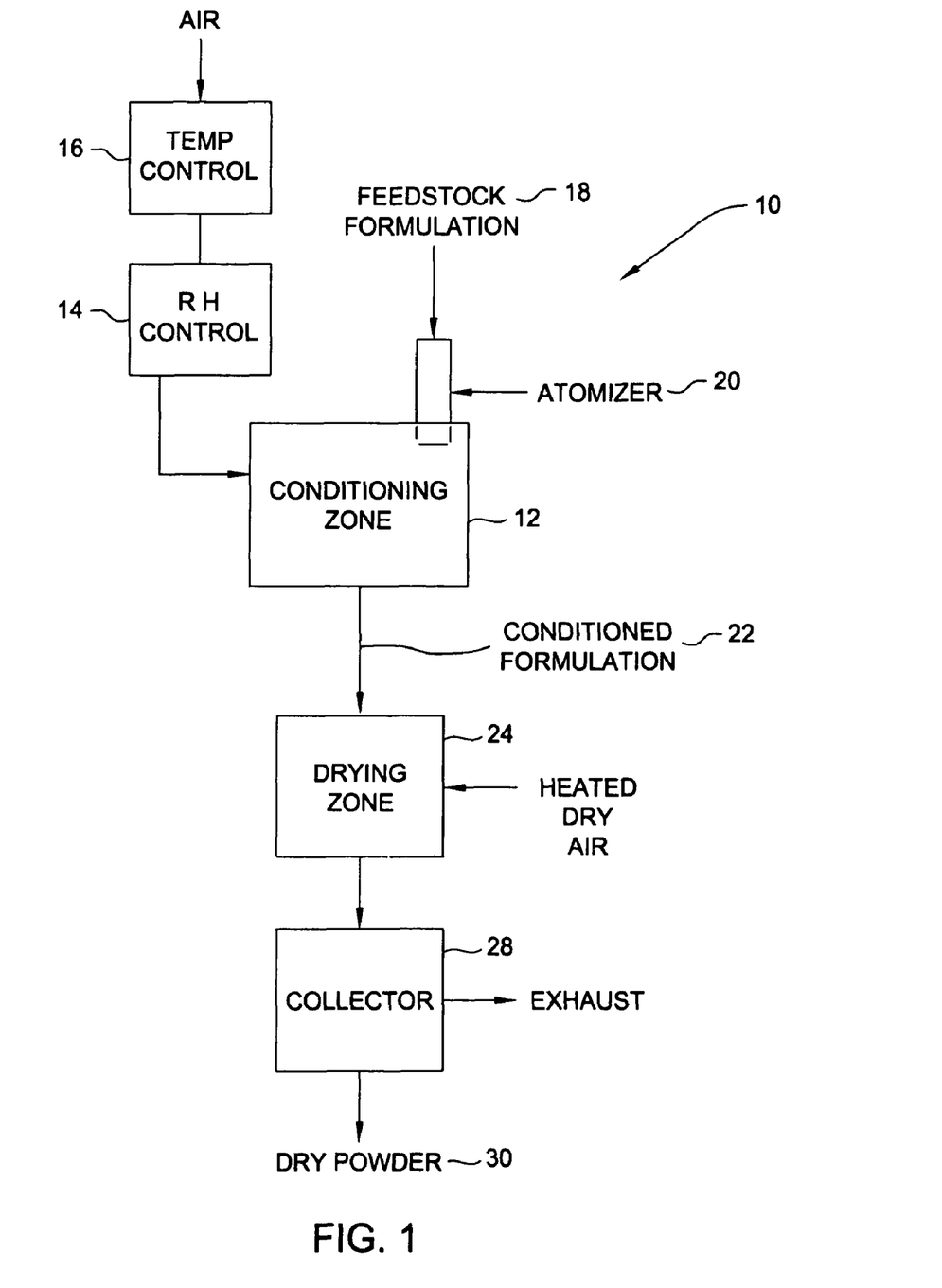
FIG. 1 is a schematic representing one embodiment of a system of the present invention for producing dry powders according to methods of the present invention.

FIG. 1 is a schematic diagram of an exemplary system for producing dry powders according to the present invention. FIG. 1 depicts a system 10 having a conditioning zone 12. A feed stock 18 is injected into conditioning zone 12 through an atomizer 20. A relative humidity controller 14 and a temperature controller 16 are included which operate to control the relative humidity and temperature of the air flow entering the conditioning zone 12. Relative humidity controller 14 may inject water into the air inlet flow to the conditioning zone 12 to increase the humidity therein. The temperature controller 16 controls the temperature within conditioning zone 12 by controlling the temperature of the air added to the conditioning zone 12.

According to a first aspect of the present invention directed to systems and methods for producing dry powders comprising increased surface concentration of surface active components, the active agent, excipient or active agent/excipient combination is dissolved or suspended in feed stock 18 at a concentration from 0.01% (w/v) to 10% (w/v), usually from 0.1% to 5.0% (w/v) and often from 1.0% to 3.0% (w/v). The formulation is atomized and then enters into conditioning zone 12. The atomized formulation remains in the conditioning zone at relative humidity and temperature levels controlled in order to minimize evaporation and allow the droplet to reach thermodynamic equilibrium wherein the surface active component reaches its equilibrium orientation at the droplet surface. According to this aspect of the invention, droplets leaving the conditioning zone maintain a majority of the solvent and thus remain in liquid state as discussed in detail below.

According to this aspect of the present invention, the conditioning zone 12 is operated to minimize slow drying rates in order to facilitate increased diffusion of surface active components, such as proteins including insulin, to the droplet surface prior to formation of a dried particle "skin" as discussed above. Preferably, the temperature in conditioning zone 12 is lowered to minimize droplet drying in the period immediately following atomization. Initial droplet drying is limited by maintaining a high relative humidity environment within conditioning zone 12 at moderate temperatures. Temperatures in conditioning zone 12 are less than 60° C., preferably less than 50° C., and most preferably 25-50° C., and relative humidities of greater than 10%, preferably greater than 20%, and most preferably greater than 25% up to 100%, are maintained in conditioning zone 12. Droplet residence time in conditioning zone 12 according to this aspect of the invention is preferably from about 0.1 second to about 20 seconds, and more preferably is from about 2 seconds to about 5 seconds. However, the specific residence time may vary depending upon the particular formulation of feed stock 18. During the residence time, atomized formulation 18 preferably remains as liquid droplets. The residence time and conditions in the conditioning zone are maintained such that the atomized formulation exiting the conditioning zone 12 remains in liquid form.

The control of temperature, relative humidity of the air added to the conditioning zone 12 and control of the residence time within conditioning zone 12 facilitates the production of exemplary dry powders by suspending the atomized feed stock 18 in liquid form for a sufficient duration to encourage increased surface enrichment of surface active components. Conditioning of the liquid droplets at minimized drying rates compared to standard spray drying systems, such as those manufactured by Buchi, Niro, APV, Yamato Chemical Company, Okawara Kakoki Company and others, facilitates the droplets reaching thermodynamic equilibrium and diffusion of the surface active components to the droplet surface. In this manner, increased solids content in the atomized feed stock 18 can be processed while enriching the surface of the dry powders produced with surface active components. Accordingly, the dry powders so produced will have a higher emitted dose as compared to those produced in a standard Buchi or Niro spray drier (see FIG. 2).

According to another aspect of the present invention directed to promoting amorphous to crystalline transformation of a spray dried formulation, the present invention provides for systems and methods for producing dry powders that are more stable than previously produced spray dried powders. Dry powders are preferably prepared by spray drying under conditions which often result in a mixed amorphous and crystalline powder. Bulk active agent, usually in crystalline form, is dissolved in a physiologically acceptable aqueous buffer, typically a citrate buffer having a pH range from about 2 to 9. Excipients may be added to the solution either in combination with the active agent or, where no active agents to be delivered, by themselves. The active agent is dissolved or suspended in a feed stock at a concentration typically from 0.01% (w/v) to 3% (w/v), usually from 0.2%-2.0% (w/v). It is to be understood that higher concentrations of active agent in the feed stock are within the scope of this invention. According to this aspect of the invention, the atomized formulation passes through at least one conditioning zone where temperature and relative humidity are controlled to provide amorphous to crystalline transformation of the formulation. According to this aspect of the invention, a majority of the liquid phase is evaporated from the atomized formulation prior to the final drying process such that the droplets entering the conditioning zone leave as partially dried particles. The partially dried particles retain sufficient moisture to act as a plasticizer and allow crystallization.

According to this aspect of the present invention, the partially dried particles are exposed to significantly increased relative humidities for prolonged residence times. According to this aspect of the invention, the temperature in conditioning zone 12 is within 35-120° C. the relative humidity in conditioning zone 12 is from 10-99% and the residence times are sufficient to allow amorphous-to-crystalline transformation to the extent where substantially no further crystallization occurs. Residence times are preferably from about one second to about 60 seconds, and more preferably is from about 2 seconds to about 20 seconds. However, the specific residence time may vary depending upon the particular formulation of feed stock 18. According to this aspect of the invention, partially dried particles exit conditioning zone 12 for further conditioning and/or final drying prior to collection. A majority of the liquid has been evaporated from the atomized formulation exiting the conditioning zone (or the last conditioning zone if multiple conditioning zones are used) prior to entering the final drying stage.

Referring back to FIG. 1, atomizer 20 operates as an inlet to conditioning zone 12. More specifically, feed stock formulation 18 is atomized by atomizer 20 and injected into conditioning zone 12, where it remains for a residence time as discussed above. For preparation of dry powders intended for inhalation, atomizer 20 produces droplets of less then 50 μm, preferably less then 30 μm, and most preferably less than 20 μm in diameter. The time that atomized formulation 18 remains in conditioning zone 12 will vary according to the size, type and number of conditioning zone(s) 12. Preferably, conditioning zone 12 is configured to provide prolonged residence times of formulation 18 within conditioning zone 12 as compared to more rapid drying environments as discussed above.

System 10 can be used with a variety of feed stock 18 to form a dry powder 30. For example, feed stock 18 may include the active agents described above alone or in combination with any of the excipients described above or the feed stock 18 may include the excipients in the absence of active agents. One or more active agents and one or more excipients may be included in the feed stock formulation. The feed stock formulation may also include a solvent or cosolvent system. The solvents may be but are not limited to water, ethanol, acetone, isopropanaol, and methanol or combinations thereof.

In one embodiment, conditioning zone 12 comprises a plug flow conditioning zone 12, i.e. a first-in-first-out (FIFO) conditioning zone. Alternatively, conditioning zone 12 may be a back mixing conditioning zone 12, i.e. a recirculation conditioning zone. Further, more than one conditioning zone 12 may be used, including combinations of FIFO and recirculation (continuous stirred tank reactors) configurations. In this manner, the residence time can be controlled by controlling the time feed stock 18 spends in the desired temperature/relative humidity environment within conditioning zone 12. In one embodiment, conditioning zone 12 comprises an elongate insulated tube (such as a glass tube) having a length of about 2 meters to about 6 meters.

For embodiments using relative humidity controller 14, controller 14 allows enough humid air into the conditioning zone 12 to control its relative humidity to be at least 10%, preferably between about 20% and about 99%.

During operation, it is preferable to monitor the temperature within system 10. Estimates of effective temperature in relative humidity environments may be extimated from a differential scanning calorimetry (DSC) thermoactivity monitor (TAM), moisture sorption and x-ray powder diffraction. In one embodiment, temperatures in conditioning zone 12 range from between about 35° C. and about 110° C. depending upon the temperature/relative humidity combination selected for an individual run.

In one embodiment, feed stock formulations of known composition and solids content are pumped through a twin fluid atomizer 20 at liquid rates of between about 2.5 to about 100.0 milliliters per minute (ml/min), often between about 2.5 and 7.0 ml/min for a laboratory scale process and about 10.0 to 100.0 ml/min for a pilot commercial scale process. Atomizer 20 gas pressures and flow rates are between about 30 pounds per square inch (psig) to about 100 psi and about 0.5 to 1.3 scfm, respectively for a laboratory scale process and about 30-130 psig and 5-20 scfm for a pilot commercial scale process.

As depicted in FIG. 1, feed stock 18 exits conditioning zone 12 and enters a dryer 24. Dryer 24 operates to further dry the atomized feed stock 18 into a dried formulation, and typically operates with a relative humidity that is significantly less than the relative humidity of conditioning zone 12. Dryer 24 has an inlet to receive conditioned feed stock 22 and an inlet to receive hot dry air. In addition, heated air (for example, about 4-9 scfm) may be added to system 10 airstream between conditioning zone 12 and dryer 24. In one particular embodiment, the temperature of the air is between about 90° C. to about 180° C., depending upon the amount of water in system 10 and the desired relative humidity/temperature combinations downstream.

Dryer 24 can have a variety of configurations within the scope of the present invention. For example, in one embodiment dryer 24 is an insulated glass chamber or tube about 2 meters to about 6 meters in length. In one embodiment, drying zone 24 is an insulated glass chamber or tube about 1 meter to about 3 meters in length. In one particular embodiment for promoting crystallinity, particle residence time in drying zone 24 is about 0.4 seconds.

Total airflow through system 10 will vary depending upon system 10 configuration, collection device, and feed stock 18 being processed. In one example, total airflow is from about 19 scfm to about 23 scfm, taking into account atomizer air, feed stock 18 and air injected into conditioning zone 12 and heated air injected into dryer 24.

The dried formulation comprises dry powder 30 that is collected in a collector 28. Collector 28 may comprise, for example, a cyclone or baghouse collector. It will be appreciated by those skilled in the art that other collectors also may be used within the scope of the present invention. Dry powder 30 preferably has a mass median diameter (MMD) from between about 0.5 microns to about 10.0 microns and a mass median aerodynamic diameter (MMAD) between about 1 and 5 microns.

Figure 3:
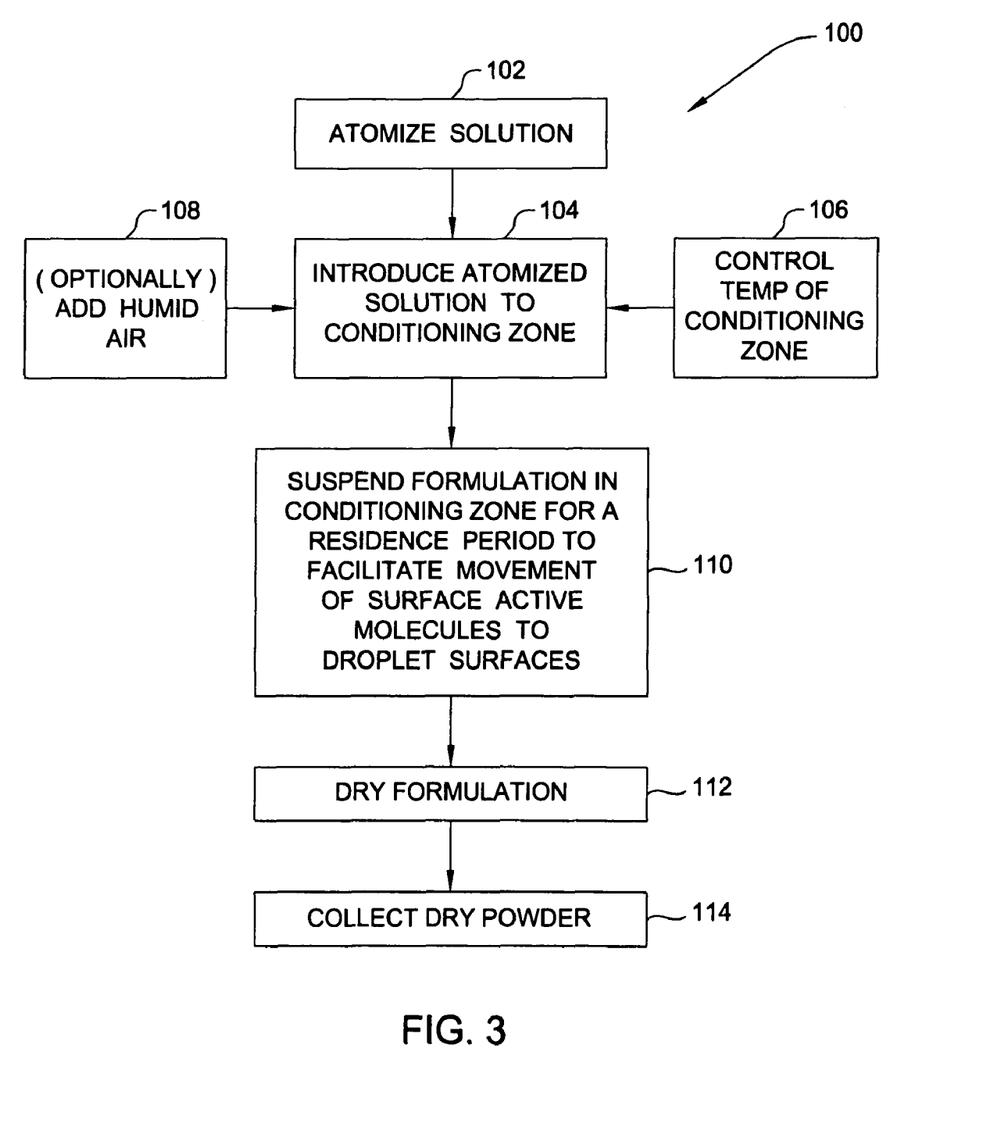
FIG. 3 is a flow chart representing a method of the present invention using the system depicted in FIG. 1.

The present invention further provides exemplary methods of producing powdered formulations using system 10. As shown in FIG. 3, one exemplary method (100) involves atomizing a feed stock (102) and introducing the atomized feed stock into a conditioning zone (104). The method includes controlling the temperature (106) within the conditioning zone and may further include adding humid air (108) to control the relative humidity within the conditioning zone. The solution is suspended (110) in the conditioning zone for a residence time to facilitate movement of surface active components to droplet surfaces. The method then includes drying the feed stock formulation (112) and collecting the dry powder (114).

In one aspect, the conditioning zone is configured to suspend the atomized droplets for a residence time in the range from about 0.1 second to about 20 seconds. In another aspect, the conditioning zone includes an elongate insulated tube having a length of at least about 1 meter. By controlling, inter alia, the conditioning zone size and the feed stock formulation flow rate through the conditioning zone, the residence time can be controlled. In one aspect, the conditioning zone includes a tank capable of suspending the feed stock formulation. In one aspect, a humidifier is coupled to the conditioning zone to control the relative humidity therein. Similarly, in another aspect the system includes a temperature controller to control the temperature of the feedstock formulation upon entry into the conditioning zone. Controlling the formulation temperature and conditioning zone relative humidity assists in the diffusion of surface active particles, in part by maintaining the atomized formulation in the liquid state in the conditioning zone.

In one aspect, the formulation is suspended in conditioning zone 12 by passing the formulation through an elongate tube of the conditioning zone. Alternatively, the formulation is suspended by circulating the formulation in a tank of the conditioning zone. Hence, a variety of conditioning zones may be used within the scope of the present invention.

Figure 4:
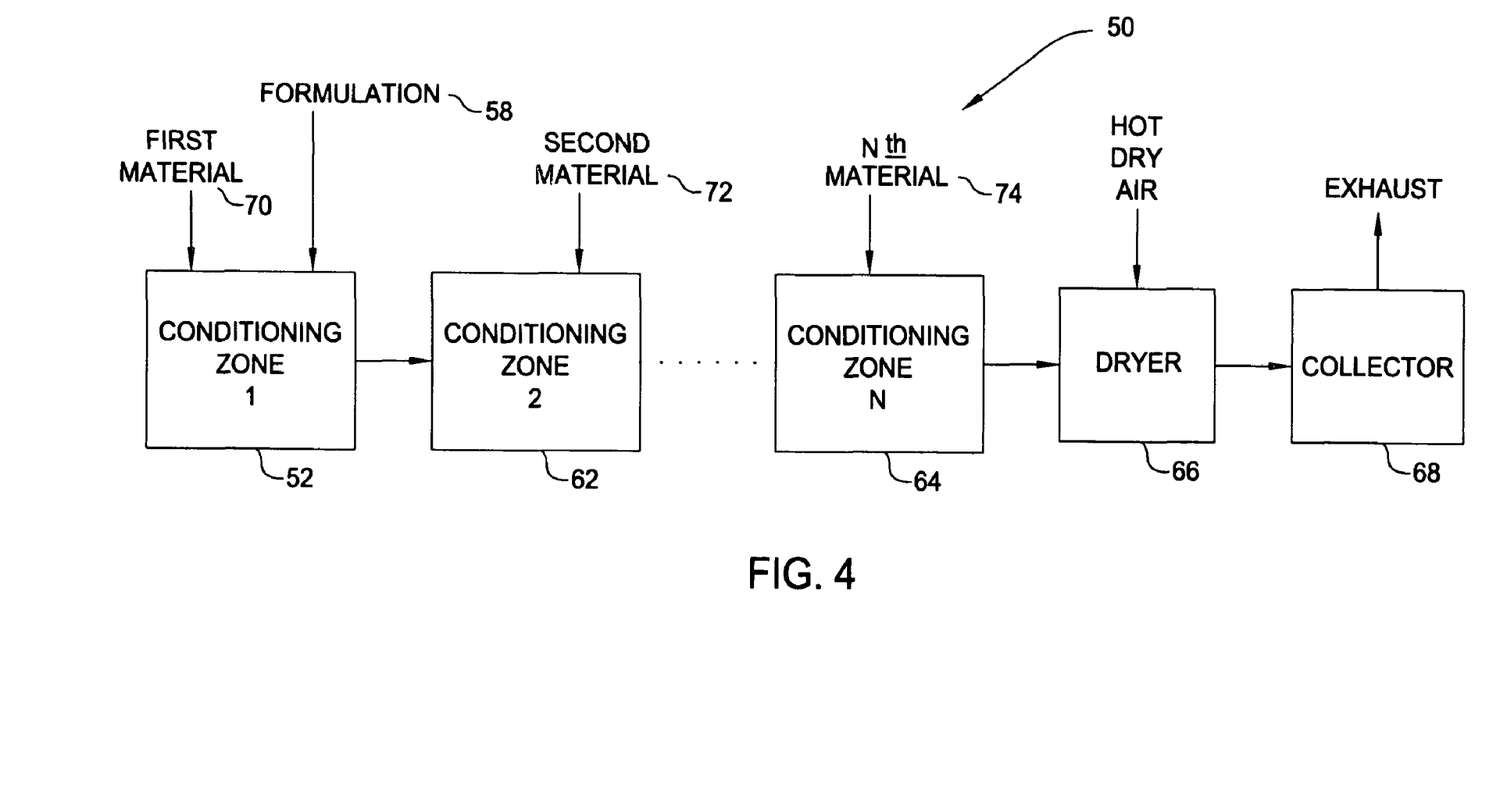
FIGS. 4-6 are schematic diagrams that represent alternative embodiments of systems of the present invention for producing dry powders according to methods of the present invention.

Turning now to FIG. 4, an alternative system 50 for producing dried powders according to alternative methods of the present invention will be described. System 50 has a first conditioning zone 52 for receipt of an atomized feed stock formulation 58. As previously noted, first conditioning zone 52 may include a monitor to monitor temperature and/or relative humidity in addition to a controller to control temperature and/or relative humidity of the air flow entering conditioning zone 52. As shown in FIG. 4, a plurality of conditioning zones are coupled in series to control the environment in which atomized formulation 58 is introduced. FIG. 4 depicts a second conditioning zone 62 up to an Nth conditioning zone 64. By using multiple conditioning zones 52, 62-64, the temperature, relative humidity and conditioning time can be controlled. Such an environment allows amorphous-to-crystalline transformation of the atomized formulations. The use of multiple conditioning zones 52, 62-64 also permits a single system 50 to change the conditioning time, as may be needed for the production of different formulations, by changing the number of conditioning zones 52, 62-64.

The use of multiple conditioning zones 52, 62-64 further enables the introduction of a variety of constituents into the flow of system 50 at appropriate locations. For example, in certain circumstances it may be desirable to introduce additional material such as solvents and solvent vapors into system 50. The introduction of such materials can occur at appropriate locations within system 50 and, more specifically, within desired conditioning zones 52, 62-64. As shown in FIG. 4, a first material 70 is inserted into conditioning zone 52, a second material 72 is introduced into conditioning zone 62, and an Nth material 74 is introduced into conditioning zone 64. The number and type of materials 70-74 introduced into system 50 of course will vary depending in part upon the formulation 58 being processed.

For example, multiple conditioning zones enable the sequential transformation and drying of constituents within formulation 58 by using cosolvents having different vapor pressures. In one embodiment, formulation 58 comprises an active agent and an excipient in a ethanol/water cosolvent. The evaporation of one cosolvent, for example the ethanol, causes solidification of components that were dissolved therein and results in the composition of the drying surface of the droplet to be enriched by those components. Next, evaporation of the remaining solvent, for example the water, results in the solidification of the ethanol soluble components. It will be appreciated by those skilled in the art that the use of water and ethanol is but one example of many cosolvents and multisolvents that may be processed in system 50. For example, to the active agent ethanol/water cosolvent formulation 58 described above, a first material 70, comprising excess ethanol, and a second material 72, comprising heated dry air may be added. As previously described, the ethanol will evaporate first, and then the water will evaporate. However, since ethanol has been added in excess, the ethanol dissolved component will remain dissolved until after the second material 72 is added. The first solvent to evaporate will determine the surface of the drying particle since the components dissolved in that solvent will solidify first. The remaining solvent(s) evaporate through that drying skin and their dissolved components solidify on the inside of the drying skin.

In one embodiment, second material 72 or Nth material 74 comprise reagents capable of reacting with the surface components of the dispersed particles forming part of formulation 58. Such reagents could provide, for example, a coating of formulation 58. Such reagents may include, but are not limited to phospholipids, saccharin, leucine and cholesterol. Materials 70-74 further may include the heated gas streams containing sublimed materials. When added to the flow of gas and formulation 58 through conditioning zones 52, 62-64 sublimed material may be deposited as a solid coating around the particle.

As shown in FIG. 4, system 50 further includes a dryer 66 for drying the formulation. Dryer 66 preferably permits the introduction of heated dry air into the flow of formulation 58 through system 50. A collector 68 operates to collect the dried particles as previously described. In system 50, the control of temperature, relative humidity and conditioning time within conditioning zones 52, 62-64 facilitates the amorphous-to-crystalline transformations of formulations 58 to produce dried particles having a higher crystalline percentage.

Figure 5:
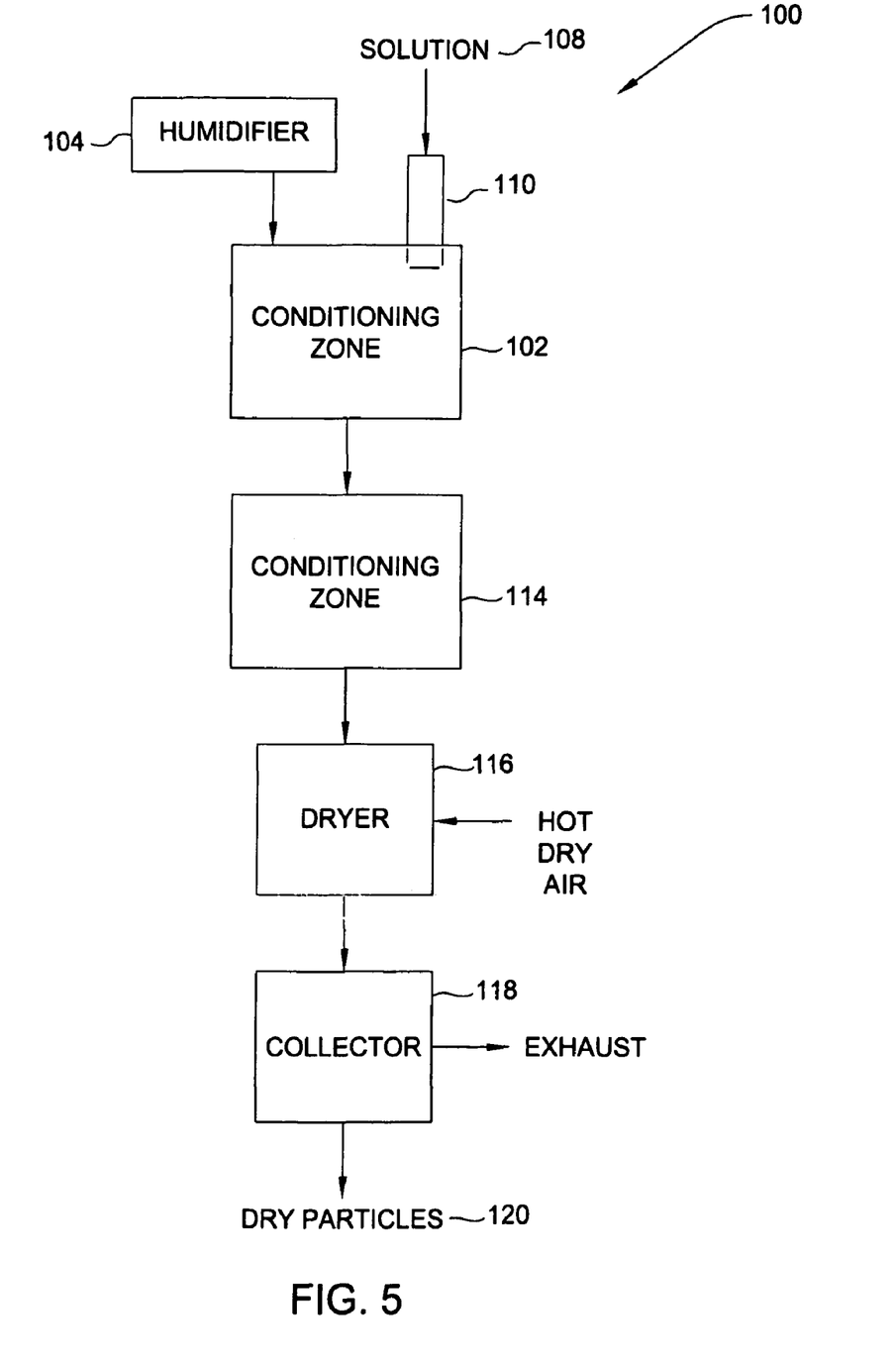

Turning now to FIG. 5, an alternative embodiment of a system 100 according to the present invention will be described. As shown in FIG. 5, system 100 includes a first conditioning zone 102 coupled to a second conditioning zone 114, which in turn is coupled to a dryer 116. A collector 118 is coupled to dryer 116 and operates to collect dry particles 120. Atomized feed stock formulation 108 is introduced into conditioning zone 102 through an atomizer 110 as previously described in order to allow diffusion of surface active components. Humidity within conditioning zone 102 is controlled using a humidifier 104. Conditioning zone 114 operates to allow amorphous-crystalline transformations as discussed above. By minimizing droplet drying for a particular time period in conditioning zone 102, and controlling moisture content of the partially dried particles for a given temperature, droplet drying for an orientational equilibrium of particle components and desired crystallinity may be attained, and greater particle stability achieved.

Figure 6:
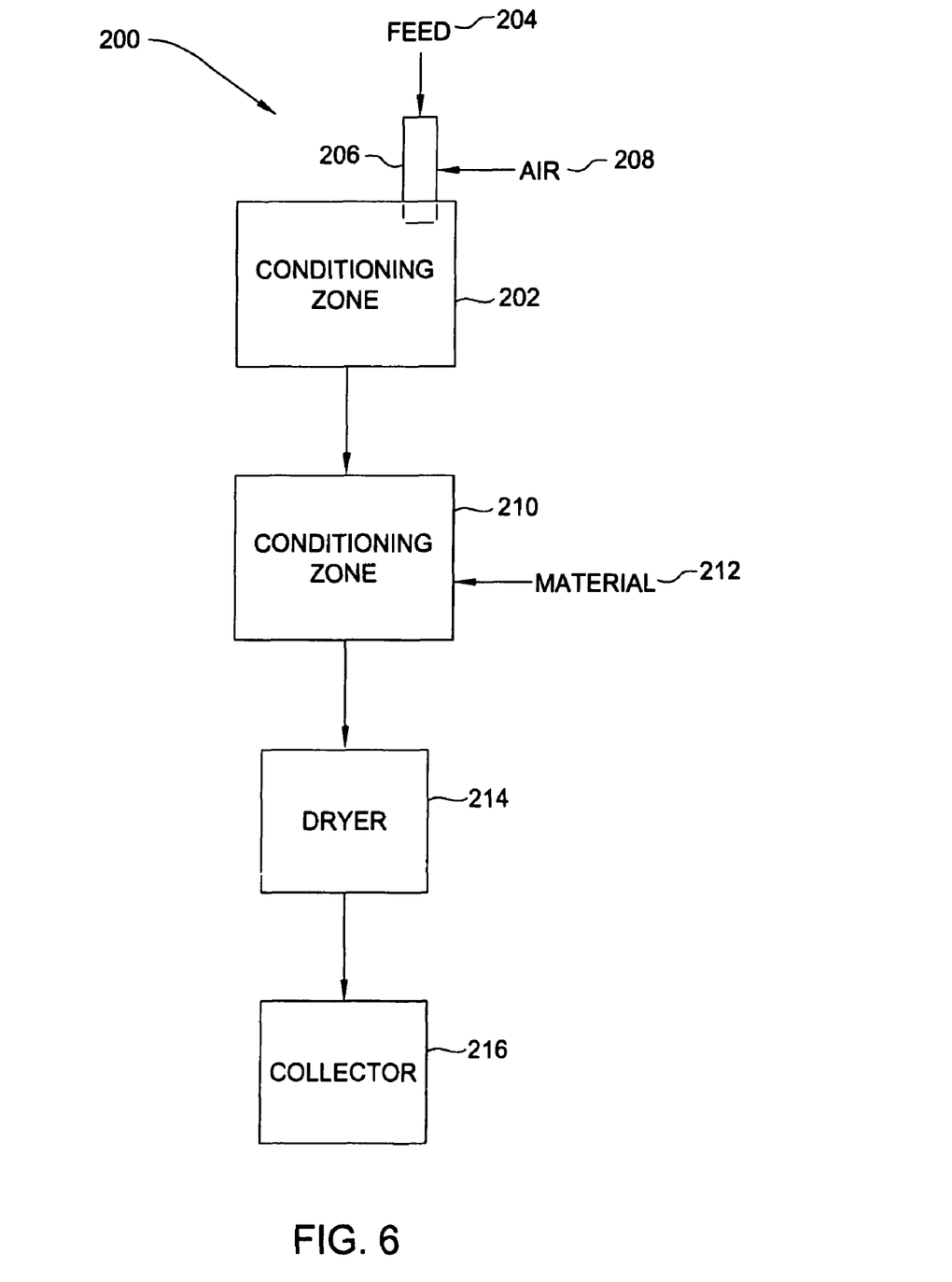

Similarly, as shown in FIG. 6, a system 200 has a first conditioning zone 202 coupled to a second conditioning zone 210. In this embodiment, an atomizer 206 inserts an atomized feed stock formulation 204 into conditioning zone 202. In some configurations, it may also be preferable to insert heated dry air 208 into conditioning zone 202. The size, shape and type of conditioning zone 202 may vary depending upon the powder being formed within system 200. After a predetermined period of time within conditioning zone 202, the formulation is transferred to conditioning zone 210 at which time a material 212 is inserted into conditioning zone 210. Material 212, as previously discussed, may comprise sublimed materials, reagents and the like. Materials 212 may be used, for example, to form a coating on particles within formulation 204. The atomized formulations 204 then are dried in a dryer 214 and collected in a collector 216 as described in conjunction with previous figures.

According to another embodiment of the present invention, any of the conditioning zones or dryers discussed above are operated at elevated pressure up to about 75 atmospheres, preferably up to 15 atmospheres, and most preferably up to about 10 atm. (150 psig). Operation at such elevated pressures provides the ability to de-couple absolute and relative humidity effects to modulate the drying kinetics and augment crystalline growth rate. Operation at elevated pressure also provides the ability to reduce the initial droplet size from the atomizer, reduce secondary atomization caused by internal droplet expansion due to dissolved gasses in the liquid, and increase the drying gas mass flow and hence powder throughput by an order of magnitude. It further provides an expanded range of gas mixing rates by the manipulation of gas jet density ratios.

For example, for a given temperature and absolute humidity, the relative humidity increases in proportion to the absolute pressure. Therefore, the relative humidity increases as the dryer system pressure increases for any given set of flow rates and temperature. The residual moisture in a dried powder is a function of formulation and the relative humidity it is in equilibrium with. This causes a significant increase in the moisture content of a powder in the dryer or collector or conditioning zone at several atmospheres pressure. Thus, decoupling of the absolute and relative humidities can be manipulated to increase the rate of crystallization for some formulations including those containing polyols such as mannitol.

The conditioning zones and/or dryer are pressurized by providing a source of pressurized gas such as air or nitrogen in communication with the conditioning zone and/or dryer. According to the invention, the pressure source is capable of providing a pressure of up to about 75 atmospheres within the conditioning zone and/or dryer, and preferably provides a pressure of up to about 15 and most preferably 10 atmospheres. The dryer may also be pressurized by providing the hot drying gas to the chamber under pressure.

In one particular aspect, the formulation includes at least about 1 percent solids content, and the dry particles have an emitted dose of at least about 60 percent. The present invention further includes dry powdered formulations produced according to the claimed methods.

The amount of active agent in the powdered formulation will be that amount necessary to deliver a therapeutically effective amount of the active agent to achieve the desired result. In practice, this will vary widely depending upon the particular agent, the severity of the condition, and the desired therapeutic effect. However, pulmonary delivery is generally practical for active agents that must be delivered in doses of from 0.001 mg/day to 100 mg/day, preferably 0.01 mg/day to 50 mg/day.

Powdered formulations suitable for use in the present invention include dry powders and particles suspended or dissolved within a propellant. The powdered formulations have a particle size selected to permit penetration into the alveoli of the lungs, that is, preferably less than 10 µm mass median diameter (MMD), preferably less than 7.5 µm, and most preferably less than 5 µm, and usually being in the range of 0.1 µm to 5 µm in diameter. The emitted dose (ED) of these powders is >30%, usually >40%, preferably >50% and often >60% and the aerosol particle size distribution is about 1.0-5.0 µm mass median aerodynamic diameter (MMAD), usually 1.5-4.5 µm MMAD and preferably 1.5-4.0 µm MMAD. These dry powders have a moisture content below about 10% by weight, usually below about 5% by weight, and preferably below about 3% by weight. Such powders are described in WO 95/24183, WO 96/32149, and WO 99/16419 which are incorporated by reference herein.

Dry powders are preferably prepared by spray drying. The active agent, excipient, or combination of active agent and excipient, is dissolved or suspended in a physiologically acceptable aqueous buffer, typically a citrate buffer having a pH range from about 2 to 9.

The dry powders may be delivered using Inhale Therapeutic Systems' dry powder inhaler as described in 5,740,794, 5,785,049, WO 96/09085 and in U.S. Patent Application Ser. Nos. 60/136,418 and 60/141,793 which are incorporated herein by reference. The dry powders may also be delivered using a metered dose inhaler as described by Laube et al in U.S. Pat. No. 5,320,094, which is incorporated by reference herein.

Other features and advantages of the invention will appear from the following description in which the preferred embodiment has been set forth in detail in conjunction with the accompanying drawings.

EXAMPLE 1

A multi-zonal spray dryer (MZD) in accordance with FIG. 1 was constructed and tested to produce a 60 percent insulin (I-016) formulation. The temperature and relative humidity of the inlet air was controlled to achieve particular conditions in the conditioning zone 12 as shown in Table 1 below. The drying airflow rate was about 10 standard cubic feet per min (scfm) to about 14 scfm.

The 60 percent insulin formulation was prepared by dissolving human zinc insulin, mannitol, sodium citrate, sodium hydroxide and glycine in deionized water for a total solids concentration as listed in Table 1. The residence time was between 3.6 and 3.8 seconds and was designed to be of sufficient length to encourage surface diffusion of insulin protein molecules. The success of the example was determined by comparing emitted dose (ED) as a function of total solids. Results and operating conditions for four test runs using solutions containing 3% solids are provided in Table 1 below. The values are plotted as triangles on the graph shown in FIG. 2 and compared with values of emitted doses for solutions of 1% to 4% solids using standard spray driers.

TABLE 1

Table 1. MZD operating conditions for spray aging of I-016 powders.

| | Formulation solution | | Conditioning zone | | Drying zone | | Cyclone | | | |
|---|---|---|---|---|---|---|---|---|---|---|
| lot # | [soln] (%) | pump (ml/min) | temp./RH (° C.)/(%) | time (sec) | temp./RH (° C.)/(%) | time (sec) | temp./RH (° C.)/(%) | Yield (%) | MMD (µm) | Moisture (%, w/w) |
| 97322 | 3 | 5 | 50/45 | 3.8 | 63/19 | 0.4 | 60/19 | 85 | 2.20 | 2.8 |
| 97381 | 3 | 7 | 35/43 | 3.7 | 68/6 | 0.4 | 66/6 | 80 | 1.48 | 3.4 |
| 97382 | 3 | 7 | 41/31 | 3.6 | 68/6 | 0.4 | 66/6 | 80 | 1.67 | 2.3 |
| 97383 | 3 | 7 | 44/27 | 3.6 | 67/6 | 0.4 | 65/6 | 90 | 1.66 | 2.3 |

The conditioning zone was an insulated glass tube about 2.1 meters in length and the drying zone was an insulated glass chamber about 0.6 meters in length. The conditioning zone temperature was monitored at a position immediately prior to the hot dry air inlet position. Temperature was nearly constant along the length of the conditioning zone (plus or minus about 2° C.). Monitored temperatures were used to calculate system relative humidity.

As shown above in Table 1, in one run (lot #97322) a 60 percent insulin formulation having about three percent solids was pumped into the conditioning zone at a rate of 5 ml/min. The conditioning zone was operated at about 50 degrees Celsius and about 45 percent relative humidity. The formulation remained in the conditioning zone for about 3.8 seconds before proceeding into the dryer. The now partially dried particles passed through the dryer in about 0.4 seconds, with the dryer operating at about 63 degrees Celsius and about 19 percent relative humidity. Dried particles were collected by a cyclone collector operating at about 60 degrees Celsius and about 19 percent relative humidity. An 85% yield was produced having an MMD of about 2.20 microns. The moisture content in the dry powder on a weight-to-weight percentage was about 2.8 percent.

Figure 2:
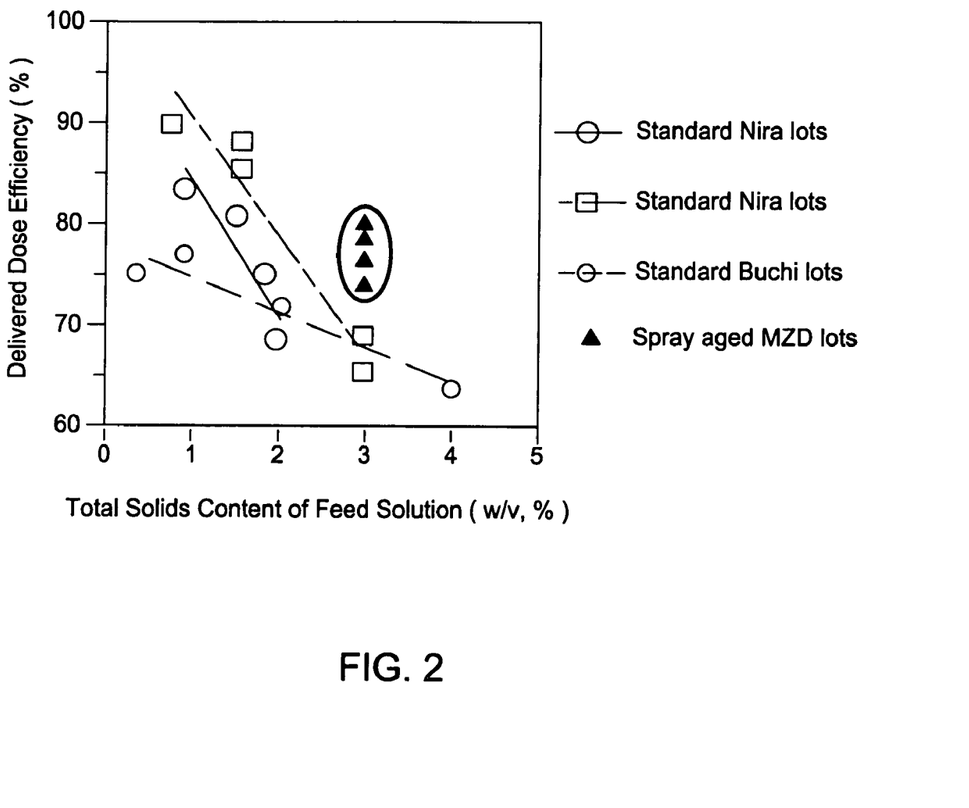
FIG. 2 is a graphic illustration indicating improved emitted dose resulting from systems and methods of the present invention.

As shown in FIG. 2, the emitted dose (ED) for the 60 percent insulin runs were all greater for a 3 percent solids composition compared to the ED for standard Niro and Buchi lots having the same percent solids composition. In this manner, the present system and methods permits increased solid content without a decrease in ED compared to standard Niro and Buchi systems.

EXAMPLE 2

A multi-zonal spray dryer (MZD) in accordance with FIG. 1 was constructed and tested to produce conditioned particles according to the invention. Two Buchi spray dryers were arranged to operate sequentially. The first Buchi (Buchi 1) operated as a humidifier. The second Buchi (Buchi 2) acted as the atomizer. A conditioning zone, an insulated glass tube about 2.1 meters in length, was attached to the outlet of Buchi 2. The drying zone was an insulated glass chamber about 0.6 meters in length attached to the end of the conditioning zone. A hot compressed dry air inlet defined the separation of the conditioning zone and the drying zone. A cyclone collector was used to collect the dry powders produced.

Aqueous solutions containing 1.5% PTH (1-34 parathyroid hormone) and mannitol were dried in the MZD according to the following procedure and in the concentrations shown in Table 2. Water was pumped into Buchi 1 at a rate of between about 9 mL/min and about 22.5 mL/min. The inlet temperature of Buchi 1 was set between about 200 and 215° C. The drying airflow rate was about 10 standard cubic feet per min (scfm) to about 14 scfm. Atomizer gas pressure and flow rate were set to 35 psi and 0.7-1.0 scfm. The outlet temperature of the humid air from Buchi 1 ranged from about 52° C. to about 72° C.

The humid air from Buchi 1 was fed into Buchi 2. The active agent formulation feed solution was further atomized into Buchi 2 at a rate of about 2.5-7 mL/min. Atomizer pressure and flow rate were set to 80-100 psi and 1.0-1.3 scfm, respectively. The temperature of the atomized formulation that reached the conditioning zone was controlled by the volume and temperature of humid air added. The conditioning zone temperature was monitored at a position immediately after formulation atomization and the hot dry air inlet position. Temperature was nearly constant along the length of the conditioning zone (plus or minus about 2° C.). Monitored temperatures were used to calculate system relative humidity. Relative humidity calculations were based on the total amount of water entering the system, conditioning zone temperature, and assumed no leaks in the system.

From the conditioning zone, the formulations entered the drying zone and remained there from between about 0.4 and 0.5 seconds. The temperature of the drying zone was measured just before the cyclone collector and was between 40 and 80° C. The temperature of the dry air was between 90 and 180° C. A cyclone collector was used for powder collection. Table 1 shows the operating conditions and product characteristics of PTH/mannitol compositions prepared according to the invention.

Table 3 shows emitted dose of the formulations.

TABLE 2

MZD operating conditions and product characteristics of PTH/mannitol lots.

| | Formulation solution | | | Conditioning zone | | Drying zone | | Cyclone | | | Water |
|---|---|---|---|---|---|---|---|---|---|---|---|
| lot # | PTH/man | [soln] (%) | pump (ml/min) | temp./RH (° C.)/(%) | time (sec) | temp./RH (° C.)/(%) | time (sec) | temp./RH (° C.)/(%) | Yield (%) | MMD (µm) | content (%, w/w) |
| 97320 | 60/40 | 1.5 | 2.5 | 67/22 | 3.3 | 72/13 | 0.5 | 70/13 | 22 | 2.11 | 0.6 |
| 97366 | 45/55 | 1.5 | 3.0 | 89/11 | 2.5 | 83/10 | 0.4 | 81/11 | 41 | 1.71 | 1.9 |

TABLE 2-continued

MZD operating conditions and product characteristics of PTH/mannitol lots.

| | Formulation solution | | | Conditioning zone | | Drying zone | | Cyclone | | | Water |
|---|---|---|---|---|---|---|---|---|---|---|---|
| lot # | PTH/ man | [soln] (%) | pump (ml/min) | temp./RH (° C.)/(%) | time (sec) | temp./RH (° C.)/(%) | time (sec) | temp./RH (° C.)/(%) | Yield (%) | MMD (μm) | content (%, w/w) |
| 97367 | " | 1.5 | 5.0 | 65/30 | 2.7 | 74/16 | 0.4 | 72/16 | 67 | 1.58 | 1.4 |
| 97368 | " | 1.5 | 5.0 | 52/57 | 2.8 | 75/16 | 0.4 | 73/16 | 75 | 2.15 | 2.1 |
| 97319B | 30/70 | 1.5 | 2.5 | 72/20 | 2.6 | 72/11 | 0.4 | 70/11 | n.d. | n.d. | n.d. |
| 97319C | " | 1.5 | 2.5 | 66/19 | 2.6 | 72/11 | 0.4 | 70/13 | 86 | 2.06 | 0.8 | n.d. = not determined

TABLE 3

Emitted doses for PTH/mannitol lots prepared with the MZD.

| Lot # | PTH/man (w/w) | n | % Left (±SD) | % Collected (±SD) | ED (%) (±SD) |
|---|---|---|---|---|---|
| 97366 | 45/55 | 5 | 5 (2) | 75 (4) | 70.9 (4.4) |
| 97367 | " | 5 | 7 (6) | 69 (4) | 64.4 (6.2) |
| 97368 | " | 5 | 5 (2) | 68 (4) | 64.5 (3.3) |
| 97320 | 60/40 | 5 | 9 (5) | 56 (8) | 50.5 (7.6) |
| 97319B | 30/70 | 10 | 3 (6) | 66 (3) | 64.3 (4.0) |
| 97319C | " | 10 | 7 (4) | 67 (4) | 62.3 (2.8) | n.d. = not determined

The amount of crystallizable components were estimated by comparison of enthalpies of crystallization ($\Delta H_c$) obtained by differential scanning calorimetry (DSC) for particles prepared according to the invention (MZD) and those prepared by conventional spray drying systems.

Compared to a similar formulation processed through a Buchi or Niro system, the multi-zonal dryer of the present invention produced a much lower $\Delta H_c$ (see Table 4). This indicates that a much higher level of crystallization occurred as a result of processing through the present invention. With increased crystallinity observed as a result of the present invention system and method, the resultant particles had a higher rate of amorphous-to-crystalline transformation during processing and thus will show a much greater storage stability than those processed in conventional manners.

TABLE 4

Thermal analysis results for PTH/mannitol powders.

| Lot # | PTH/man (w/w) | Spray drier | Outlet/Drying zone temp. | $\Delta H_o^i$ (J/g) |
|---|---|---|---|---|
| 97320 | 60/40 | MZD | 72 | 6.9 |
| 97040 | " | Büchi | 65 | 49.6 |
| 97366 | 45/55 | MZD | 83 | 4.6 |
| 97367 | " | MZD | 74 | 7.6 |
| 97368 | " | MZD | 75 | 8.3 |
| 97189 | " | Büchi | 60 | 11.5 |
| 97319B | 30/70 | MZD | 72 | 11.5 |
| 97319C | " | MZD | 72 | 10.5 |
| 97141 | " | Büchi | 56 | 9.1 |
| B1104-4 | " | Niro | 75 | 8.6 |

EXAMPLE 3

The MZD of Example 5 was used to spray dry a 1.5% solution of 85% mannitol and 15% citrate. Operating conditions and product characteristics are shown in Table 5. Particle sizes (mass median diameter, MMD) were determined by centrifugal sedimentation (Horiba) and moisture contents were determined by Karl Fisher titration.

TABLE 5

MZD operating conditions and product characteristics of placebo (X-001) lots.

| | Formulation solution | | Conditioning zone | | Drying zone | | Cyclone | | | Water |
|---|---|---|---|---|---|---|---|---|---|---|
| lot # | [soln] (%) | pump (ml/min) | temp./RH (° C.)/(%) | time (sec) | temp./RH (° C.)/(%) | time (sec) | temp./RH (° C.)/(%) | Yield (%) | MMD (μm) | content (%, w/w) |
| 97321 | 1.5 | 2.5 | 66/23 | 2.6 | 72/11 | 0.4 | 70/11 | 42 | 2.45 | 1.2 |
| 97369 | 1.5 | 5 | 54/51 | 2.8 | 76/15 | 0.4 | 74/16 | 84 | 5.96[1] | n.d. |
| 97370 | 1.5 | 7 | 46/76 | 2.9 | 67/22 | 0.4 | 65/23 | n.d. | 5.50[1] | n.d. |
| 97371 | 1.5 | 5 | 41/99 | 2.9 | 68/21 | 0.4 | 66/22 | n.d. | 4.71[1] | n.d. |

[1]particle fusion observed for these lots;
n.d. = not determined

The emitted dose of the first lot stored for 5 months in a dry box showed less than a 10% drop as compared to greater than 25% drop for powders produced by conventional spray drying. This further indicates the stability of powders produced in the multizonal dryer.

The invention has now been described in detail. However, it will be appreciated that certain changes and modifications may be made. Therefore, the scope and content of this invention are not limited by the foregoing description rather the scope and content are to be defined by the following claims.

We claim:

1. A system for producing dry powders, the system comprising:
    an atomizer for producing droplets of a pharmaceutical formulation, said droplets having a diameter of less than 50 microns;
    at least one conditioning zone coupled to the atomizer to receive said droplets;
    a dryer coupled to the conditioning zone to dry the droplets exiting the conditioning zone; and
    a collector to collect the dried formulation in powder form
    wherein the conditioning zone comprises a humidity and/or temperature controller to control the conditions in the conditioning zone so that the droplets dry more slowly in the conditioning zone than in the dryer.

2. A system as in claim 1, further comprising a humid air inlet coupled to the conditioning zone to control the relative humidity within the conditioning zone.

3. A system as in claim 1, wherein the at least one conditioning zone comprises a plurality of conditioning zones coupled in series with each other, with each of the conditioning zones having an airflow inlet.

4. A system as in claim 1, wherein the collector is selected form the group consisting of a cyclone and a baghouse.

5. A system as in claim 1, wherein the controller is a temperature controller to control the temperature of the air upon entry into the conditioning zone.

6. A system as in claim 1, wherein the conditioning zone is configured to suspend the atomized formulation for a residence time in the range from about 0.1 second to about 60 seconds.

7. A system as in claim 1, wherein the conditioning zone comprises an elongated insulated tube having a length of at least about 1 meter.

8. A system as in claim 1, wherein the conditioning zone comprises a tank having a circulation mechanism to suspend the formulation.

9. A system as in claim 1, wherein the droplets have a diameter of less than 20 microns.

10. A system for producing dry powders, the system comprising:
    an atomizer for producing droplets of a pharmaceutical formulation, said droplets having a diameter of less than 50 microns;
    a first conditioning zone coupled to the atomizer to receive said droplets;
    a humid air inlet coupled to the conditioning zone to control the relative humidity within the conditioning zone;
    at least one additional conditioning zone coupled in series with the first conditioning zone with each conditioning zone having an airflow inlet;
    a dryer coupled to the conditioning zone to dry the formulation exiting the conditioning zone; and
    a collector to collect the dried formulation in powder form.

11. A system as in claim 10, wherein the collector is selected form the group consisting of a cyclone and a baghouse.

12. A system as in claim 10, further comprising a temperature controller to control the temperature of the air upon entry into the first conditioning zone.

13. A system as in claim 10, wherein the droplets have a diameter of less than 20 microns.

* * * * *